US007070582B2

(12) United States Patent
Freyman et al.

(10) Patent No.: US 7,070,582 B2
(45) Date of Patent: Jul. 4, 2006

(54) INJECTION DEVICES THAT PROVIDE REDUCED OUTFLOW OF THERAPEUTIC AGENTS AND METHODS OF DELIVERING THERAPEUTIC AGENTS

(75) Inventors: Toby Freyman, Watertown, MA (US); Wendy Naimark, Cambridge, MA (US); Tim Mickley, Elk River, MN (US); Samuel J. Epstein, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 314 days.

(21) Appl. No.: 10/215,034

(22) Filed: Aug. 9, 2002

(65) Prior Publication Data

US 2004/0030282 A1 Feb. 12, 2004

(51) Int. Cl.
*A61M 5/32* (2006.01)

(52) U.S. Cl. ........................ 604/272; 604/239; 604/176; 604/119; 604/121

(58) Field of Classification Search ................ 604/35, 604/40, 43, 44, 117, 264, 164.06, 272–274, 604/239, 902, 174, 176, 158, 164.01, 164.02, 604/164.04, 167.01, 118, 119, 121; 606/167, 606/172; 607/119, 120
See application file for complete search history.

(56) References Cited

U.S. PATENT DOCUMENTS

| | | | |
|---|---|---|---|
| 3,492,992 A * | 2/1970 | Kurtz | ........................ 604/272 |
| 4,540,402 A | 9/1985 | Aigner | |
| 4,735,611 A * | 4/1988 | Anderson et al. | ........... 604/130 |
| 4,737,146 A | 4/1988 | Amaki et al. | |
| 4,790,817 A * | 12/1988 | Luther | ........................ 604/509 |
| 4,791,937 A * | 12/1988 | Wang | ........................ 600/565 |
| 4,824,433 A * | 4/1989 | Marz et al. | ................... 604/21 |
| 4,861,341 A * | 8/1989 | Woodburn | .................. 604/175 |
| 4,966,586 A * | 10/1990 | Vaillancourt | ........... 604/167.01 |
| 5,178,611 A | 1/1993 | Rosenberg | |
| 5,306,239 A * | 4/1994 | Gurmarnik et al. | ......... 604/512 |
| 5,364,373 A * | 11/1994 | Waskonig et al. | ........... 604/272 |
| 5,630,802 A * | 5/1997 | Moellmann et al. | ... 604/164.01 |
| 5,817,072 A | 10/1998 | Lampropoulos et al. | |
| 6,004,302 A * | 12/1999 | Brierley | ........................ 604/264 |
| 6,077,248 A * | 6/2000 | Zumschlinge | .......... 604/167.01 |
| 6,203,532 B1 * | 3/2001 | Wright | ........................ 604/264 |
| 6,416,510 B1 | 7/2002 | Altman et al. | |
| 6,491,670 B1 * | 12/2002 | Toth et al. | .................. 604/264 |

(Continued)

FOREIGN PATENT DOCUMENTS

GB          1 284 537          8/1972

(Continued)

*Primary Examiner*—Cris Rodriguez
(74) *Attorney, Agent, or Firm*—Kenyon & Kenyon LLP

(57) ABSTRACT

Injection devices are provided, which reduce potential outflow of therapeutic agents from an injection site. Devices are provided having at least a first lumen containing one or more therapeutic agents and a second lumen containing a second material for injection into tissue. Other devices are provided having an inner lumen with an injection needle to inject a therapeutic agent and an outer lumen that provides a vacuum seal between the injection needle and the needle track. Further provided are methods of delivering a therapeutic agent to tissue.

11 Claims, 8 Drawing Sheets

U.S. PATENT DOCUMENTS

| | | | |
|---|---|---|---|
| 6,530,902 B1 * | 3/2003 | Jonkman | 604/164.01 |
| 6,641,564 B1 * | 11/2003 | Kraus | 604/164.1 |
| 6,733,515 B1 * | 5/2004 | Edwards et al. | 606/214 |
| 2002/0169377 A1 * | 11/2002 | Khairkhahan et al. | 600/433 |
| 2002/0177864 A1 * | 11/2002 | Camrud | 606/167 |
| 2003/0158519 A1 * | 8/2003 | Epstein et al. | 604/116 |
| 2004/0082906 A1 * | 4/2004 | Tallarida et al. | 604/43 |
| 2004/0116856 A1 * | 6/2004 | Woehr et al. | 604/110 |

FOREIGN PATENT DOCUMENTS

WO     WO 01/62141     8/2001

* cited by examiner

INJECTION DEVICES THAT PROVIDE REDUCED OUTFLOW OF THERAPEUTIC AGENTS AND METHODS OF DELIVERING THERAPEUTIC AGENTS

FIELD OF THE INVENTION

The present invention relates to injection devices that provide reduced leakage of therapeutic agents from an injection site resulting in increased agent uptake. According to embodiments of the present invention injection devices are provided having at least two lumens containing one or more therapeutic agents in at least one lumen and at least a second material for injection in at least one other lumen. Other embodiments include injection devices having at least one lumen containing one or more therapeutic agents and an outer lumen adapted to provide a vacuum seal between an injection needle and the needle track it creates.

The present invention also relates to methods for delivering therapeutic agents to a tissue. Embodiments of the present invention include injecting at least one therapeutic agent into tissue and injecting at least one second material to the tissue. Other embodiments include creating a vacuum between an injection needle and the needle track it creates to reduce potential leakage of the therapeutic agent.

BACKGROUND OF THE INVENTION

The treatment of disease such as vascular disease by local pharmacotherapy presents a means of delivering therapeutic drug doses to target tissues while minimizing systemic side effects. Such localized delivery of therapeutic agents has been proposed or achieved using medical devices such as catheters, needle devices and various coated implantable devices such as stents.

The localized delivery of therapeutic agents using needle devices has the advantages of precise placement and accurate control over the volume and rate of delivery. However, delivery using needle devices creates a needle track, which allows leakage or outflow of the therapeutic agent.

SUMMARY OF THE INVENTION

Embodiments of the present invention include injection devices that include at least a first lumen containing at least one therapeutic agent for injection into a tissue and a second lumen containing at least a second material for injection into the tissue. The depth and deployment of each lumen into tissue is controlled together or preferably independently from one another. The injection device optionally includes a third lumen containing a third material for injection into the material.

In other embodiments, the present invention includes injection devices that include an injection needle at a distal end of an inner lumen adapted to inject one or more therapeutic agents into tissue, an outer lumen adapted to provide a vacuum seal between the injection needle and a needle track it creates, and a vacuum-creating device for creating a vacuum in the outer lumen. These devices optionally include one or more gaskets to aid in forming the seal.

In other embodiments, the invention includes methods of delivering one or more therapeutic agents to tissue with an injection device. These methods include injecting at least one therapeutic agent into tissue, preferably tissue of a mammal, from a first lumen of an injection device and injecting at least one second material into the tissue from a second lumen of the injection device. The second material may be injected after, before, or substantially concurrently with injection of the therapeutic agent. The composition and amount of the second material and timing of its injection with respect to the injection of the therapeutic agent, are selected so as to reduce leakage of the therapeutic agent(s) from the injection site.

Further embodiments of the present invention include other methods of delivering therapeutic agent(s) to tissue. These methods include deploying a needle from a needle injection device at the distal end of an inner lumen into tissue, thus forming a needle track; establishing a vacuum in an outer lumen of the injection device to create a vacuum seal between the needle track and the needle; injecting at least one therapeutic agent into tissue from the inner lumen; and releasing the vacuum seal.

DETAILED DESCRIPTION

Figure 1:
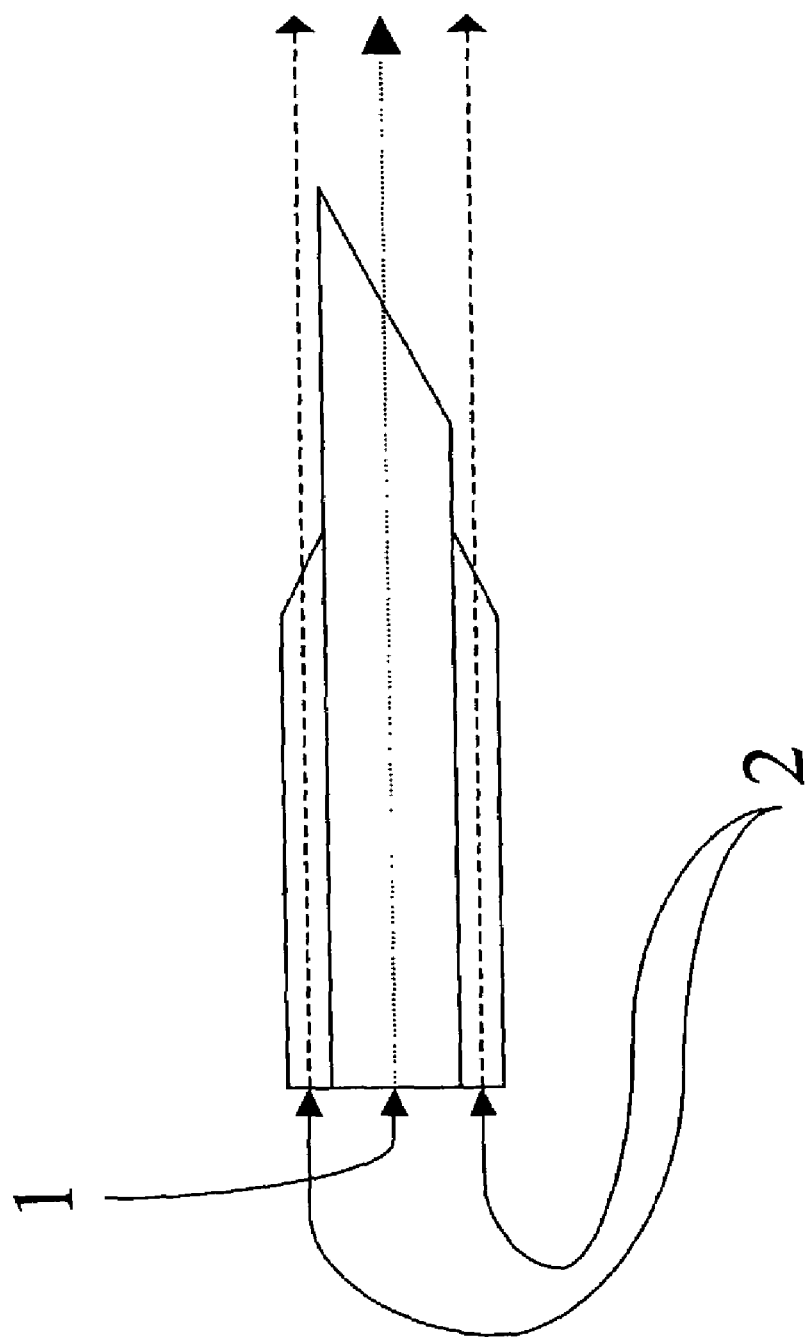
FIG. 1 depicts an injection device according to the present invention having a first lumen 1 containing at least one therapeutic agent and a second lumen 2 containing at least one second material outside the first lumen.

When therapeutic agents are delivered to target tissue with an injection device such as a needle, leaking and dispersion often result upon removal of the device form the tissue. For example, a needle track is formed in tissue after a therapeutic agent has been injected into a tissue with an injection device and subsequently removed from the tissue. Therefore, where an injection is performed via a needle, there is potential for leakage of the administered therapeutic agent along the needle track left by needle withdrawal.

This problem is exacerbated in situations where the therapeutic agent is injected into the tissue of an organ that undergoes expansion and contraction, such as the heart. In such cases, the organ wall thins during organ expansion, thus facilitating the leakage of previously-injected therapeutic agent from the organ tissue through the needle track and thereby decreasing the actual dose of therapeutic agent delivered to the target site and increasing systemic distribution of the drug. Thus, the efficiency of endocardial injection devices, for example, to deliver therapeutic agents to treat heart disease, in particular, is limited by poor retention of the therapeutic agent within tissue. As an example of the problem, it is estimated that less than 10% of cells delivered through endocardial injections are retained.

The present invention decreases the potential leakage of therapeutic agent by providing injection devices and methods that inhibit loss of injected therapeutic agent.

Injection Devices

The present invention relates to injection devices that provide reduced leakage of therapeutic agents from an injection site preferably resulting in increased efficiency or agent uptake.

The invention is described herein with specific reference to an injection needle as the injection device. Examples of specific devices incorporating injection needles, and thus within the scope of the invention, include needle injection catheters, hypodermic needles, biopsy needles, ablation catheters, cannulas and any other type of medically useful needle. It will be understood by one of ordinary skill in the art that other injection devices are contemplated and are within the scope of the invention. Specifically, any device competent to penetrate or separate tissue is contemplated, particularly those that create an opening through which a delivered agent may escape or "leak out," including for example, a lumen in the device with walls that are shaped such that it can penetrate or separate tissue. Nonneedle injection devices are also contemplated by the present invention. Examples of non-needle injection devices include, but are not limited to, transmural myocardial revascularization (TMR) devices and percutaneous myocardial revascularization (PMR) devices or any other device capable of wounding or creating a channel or crater in tissue. Further examples of suitable injection devices include ablation devices and needle-free injectors which propel fluid using a spring or pressurized gas, such as carbon dioxide injection devices.

According to embodiments of the present invention, the injection devices include at least two lumens. One or more therapeutic agents is contained in at least one lumen and at least a second material for injection in at least one other lumen.

The term "therapeutic agent" as used herein includes one or more "therapeutic agents" or "drugs." The terms "therapeutic agents" and "drugs" are used interchangeably herein and include pharmaceutically active compounds, nucleic acids with and without carrier vectors such as lipids, compacting agents (such as histones), virus (such as adenovirus, adeno-associated virus, retrovirus, lentivirus and a-virus), polymers, hyaluronic acid, gene therapies, proteins, cells, stem cells and the like, or combinations thereof, with or without targeting sequences. The injection administered in accordance with the invention includes the therapeutic agent(s) and solutions thereof Specific examples of therapeutic agents used in conjunction with the present invention include, for example, pharmaceutically active compounds, proteins, cells, stem cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

Preferred therapeutic agents according to the present invention include one or more of the following therapeutic agents: cells, stem cells, virus, protein, drug, enzymes, or combinations thereof Organs and tissues that may be treated by the methods of the present invention or using the injection devices of the present method include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone. Preferably, the tissue is myocardium, tunica media, tunica adventitia, and/or cardiac valve tissue.

The therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

Therapeutic agents may be directly injected into tissue, or may be delivered in a solution or other form and may be delivered via a carrier. Therapeutic agents may be delivered for example via microspheres that are injected into the tissue, rather than injecting therapeutic agents directly into the tissue. In preferred embodiments, therapeutic agents may be injected via microspheres into muscle tissue. Injecting therapeutic agents via microspheres may result in sustained release or delivery of the drug. Direct injection of therapeutic agents may represent an effective means to treat the entire myocardium. Injected agents tend to disperse throughout the myocardium into uninjected areas. Thus, the number of injections that is necessary in order to deliver therapeutic agents to a specific area of tissue may be decreased.

In preferred embodiments, therapeutic agents are delivered to muscle tissue by injecting a therapeutic agent directly into the muscle tissue. In more preferred embodiments, the muscle tissue is heart tissue.

The second material may be any material that when injected into or near a tissue may reduce in any way, outflow of therapeutic agent from an injection site in tissue. Examples of suitable second materials according to the present invention include, for example phosphate buffered saline (PBS), ethanol, low molecular weight polyethylene glycols (PEGs), low concentration protein gels, anionic solutions such as alginate (with or without $CaCl_2$), sodium chloride solution, hyaluronan, chitin, and heparin, saline, contrast medium, protein gel, carboxymethycellulose, platelets, potassium metaphosphate polymers, precipitation solutions (such as SAIB), and combinations thereof.

The second material(s) are preferably selected based at least in part on their physical, chemical and electrochemical properties. For example, the second material may be viscous, thus providing a physical barrier to outflow of therapeutic agent or it may be relatively inviscid thus "washing" much of the agent into the tissue. A viscous second material may be advantageously delivered before the therapeutic agent is delivered for example, so that as the therapeutic agent is delivered, much of it is kept from leaking out of the needle track opening by the viscous material. Preferred second materials according to such embodiments include, for example, low molecular weight PEGs, low concentration protein gels, cross-linked alginate gels and combinations thereof.

Figure 3:
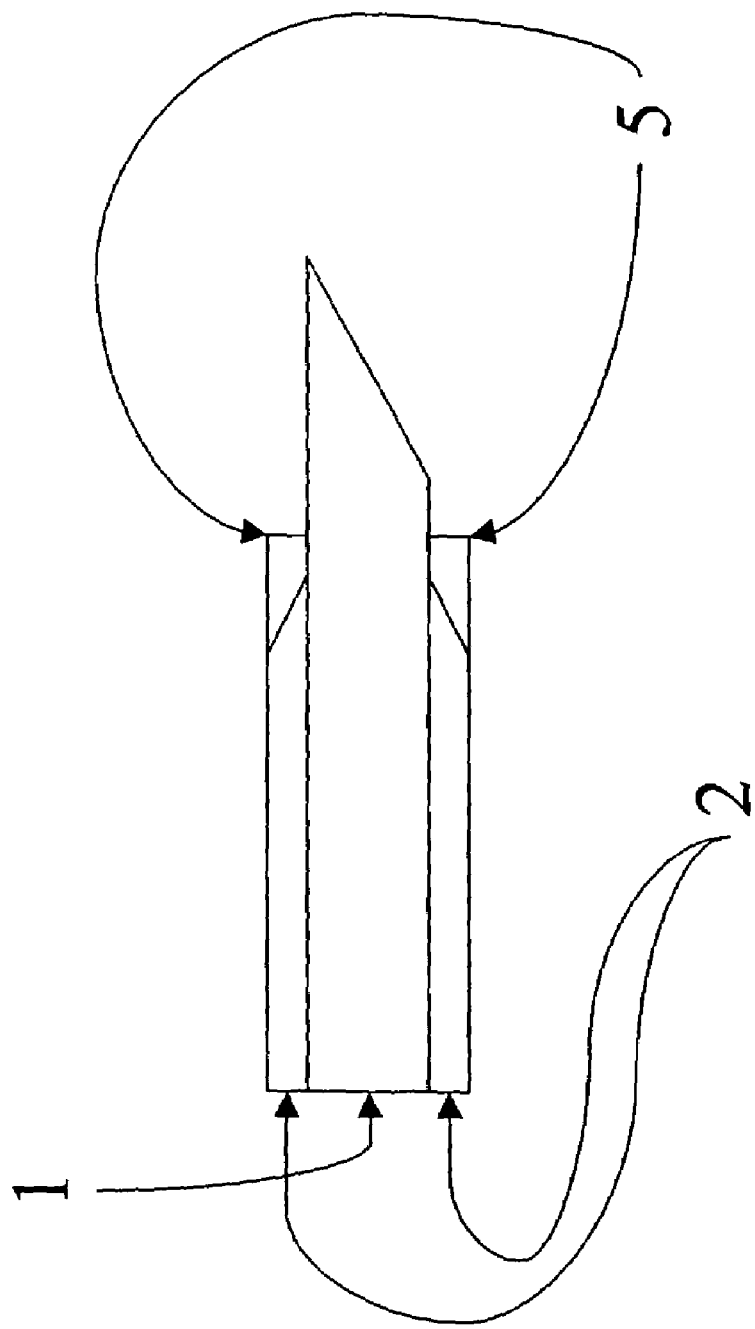
FIG. 3 depicts another injection device according to the present invention. In this embodiment the second material is relatively viscous and provides resistance to outflow of therapeutic agent.
Figure 4:
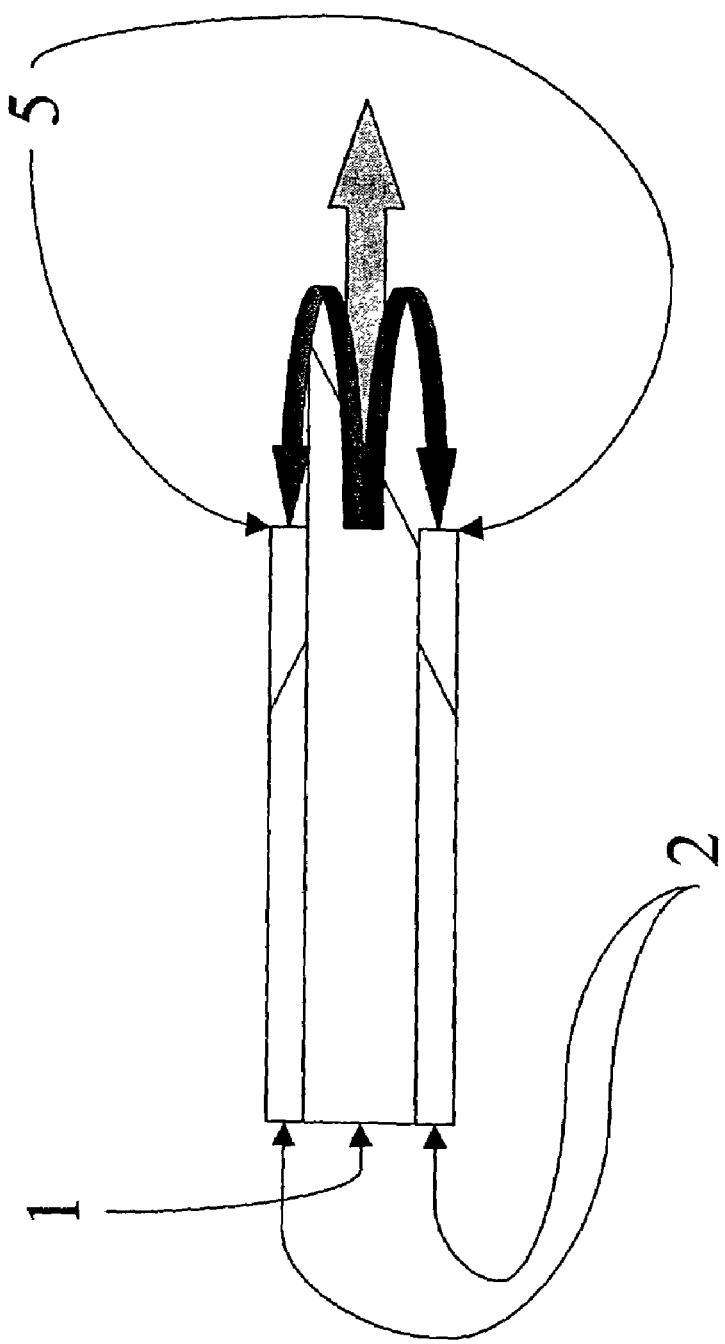
FIG. 4 depicts the injection device of FIG. 3 having a second material 5 blocking outflow of therapeutic agent.

In embodiments in which the second material is relatively viscous, the second material is preferably delivered before, and preferably proximal to the agent, so there is a resistance to flow out of the needle track. See for example FIG. 3 in which lumen 2 is activated and the second material is released from the lumen (either into, partially into, or outside of the tissue). The released second material 5 then provides resistance to outflow of the therapeutic agent from the tissue after lumen 2 is activated and the therapeutic agent is injected into tissue. As shown in FIGS. 3 and 4, the viscous second material 5 preferably provides a resistance to the therapeutic agent flowing back out of the needle track after it is released from lumen 2.

The second material may act for example as a barrier trapping agent at the distal end of the needle track, relatively deep within the myocardium. According to these embodiments, the second material is preferably administered in an amount that may be sacrificially lost through back-leakage out the needle track, without substantial loss of the therapeutic agent out of the needle track. A preferred second material according to these embodiments include for example, PBS, low concentration protein gels and the like. In addition to improving retention of the agent, preferably, the second material facilitates tissue penetration and agent distribution, preferably ultimately achieving a larger treatment zone than may have been achieved without the second material.

In embodiments in which a second material that is relatively miscible with the agent, the second material is preferably delivered simultaneously with the agent, forcing much of the agent to go and remain relatively deep in the tissue (as compared to the second material) during delivery.

According to embodiments of the invention, the second materials may include formulations that are substantially immiscible with the therapeutic bolus. Such materials may be used for example, as driving forces for therapeutic agent retention and penetration into the tissue. An example of these embodiments includes for example, delivering negatively charged plasmid DNA as the therapeutic agent and 10–100× anionic solution, such as alginate, hyaluronan, chitosan, potassium metaphosphate, glycosaminoglycan solution and the like as the second material.

The depth and deployment of each lumen into tissue is controlled together or independently from one another. Preferably, the depth and deployment of each lumen is controlled independently from one another. Such a device having independently controlled lumens is preferably controlled manually or by some control device, such that one may determine which lumen to deploy first, how far into the tissue or away from the tissue the therapeutic agent or second material should be injected, and the tining of each injection, such as whether to deploy the lumens and inject their contents simultaneously or how soon after one deployment, the other lumen is deployed. The order, depth and timing of deployment should be determined by those skilled in the art depending on various factors such as the composition of the therapeutic agents (and/or their carriers) and the second materials (including consideration of their physical characteristics, such as their relative viscosities and miscibility with each other) and the organ being injected.

The delivery of the second material may vary spatially or temporally from the delivery of the therapeutic agent as may be determined by one skilled in the art for any desired purpose, including for example, in order to improve retention of the therapeutic agent. For example, according to embodiments of the invention, the second material is delivered proximally to the therapeutic agent, which effectively washes it into the tissue. However, the temporal delivery of the second agent with respect to the first may be varied.

According to preferred embodiments, at least two lumens extend the length of a catheter which houses them, and the lumens are controlled mechanically via a proximal handle.

A first lumen may be positioned in any way with respect to the second lumen and any additional lumens, which could achieve any reduction of therapeutic agent outflow from an injection site in tissue given certain therapeutic agents (including the carrier) and second materials. For example, according to certain embodiments, the first lumen is within a second lumen. According to other embodiments the first lumen is adjacent to a second lumen (either contacting each other or not contacting each other).

FIG. 1 shows a needle injection device according to certain embodiments of the present invention, which may be used to deliver therapeutic agent to tissue by injecting the therapeutic agent into tissue. According to these embodiments, one or more therapeutic agents contained within lumen 1 are delivered to a tissue when lumen 1 is deployed into the tissue. One or more second materials within lumen 2 are delivered to the tissue when lumen 2 is deployed to the tissue. Lumen 2 may be deployed after, before or concurrently with lumen 1.

Figure 2:
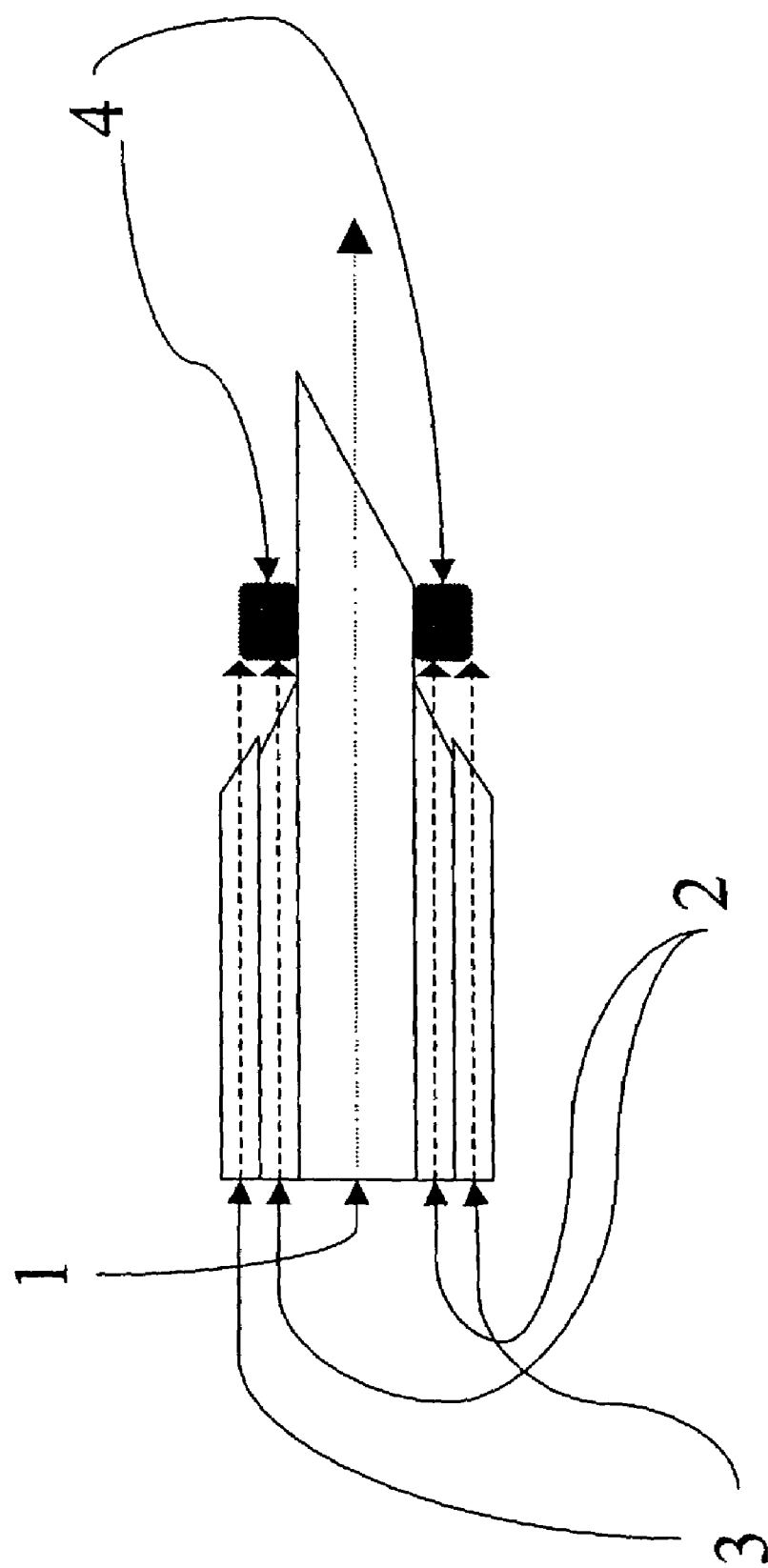
FIG. 2 depicts an injection device according to the present invention having a third lumen containing a third material for injection, where the second material and third material combine to form a plug 4.

The injection device optionally includes a third lumen 3 as depicted in FIG. 2 containing a third material for injection into the material. The third lumen may be positioned in any way with respect to the first and second lumens so as to achieve any reduction in therapeutic outflow. For example, the third lumen may be outside the second lumen as shown in FIG. 2 or adjacent to (contacting or not contacting) the second lumen. Preferably, the depth and deployment of the third lumen and any further lumens are independently controllable.

The third material may be any material that when injected into or near a tissue may reduce in any way, outflow of therapeutic agent from an injection site in tissue. Examples of suitable third materials according to the present invention include, for example crosslinking agents, polymerization initiators, surfactants, gel promoting substances, pH increasing or decreasing solutions, biologically active molecules, and combinations thereof. Preferred third materials include, for example, divalent cations, $CaCl_2$, thrombin, NaCl, potassium metaphosphate, sodium alginates, fibrin, fibrinogen, and fibronectin.

According to embodiments of the present invention having a third lumen, the third lumen is adapted such that when it is deployed it releases a third material. Preferably the third material comprises a material that when contacted with the second material, the third and second material interact to form a plug. For example, as shown in FIG. 2, a second lumen 2 is deployed releasing a second material and a third lumen 3 is deployed releasing a third material, and when the second and third materials contact one another they form a plug 4, which functions to reduce outflow of the therapeutic agent (injected into tissue when lumen 1 is deployed) from the injection site. The plug may be for example, solid or semi-solid and may be formed in the needle track or outside the needle track, for example around the needle track or in the mouth of the needle track. Preferably, the therapeutic agent is injected into tissue first and thereafter the second and third materials are injected or released either simultaneously or one after the other. Alternatively the second and third materials are released first to form a plug around the injection site and then the therapeutic agent is injected. Preferred second and third materials according to these embodiments include, for example alginate solutions, sodium alginate, calcium chloride, divalent cations, platelets and fibrin.

Additional lumens containing for example, therapeutic agents, second, third or further ingredients are contemplated herein.

Flow of the second material into the needle track and the physical barrier created by the outer lumen itself preferably also improve the retention of the therapeutic agent in the tissue.

According to other embodiments of the present invention, the injection devices are adapted such that the timing of the delivery and the amount and type of therapeutic agent and second material may be selected to improve retention of therapeutic agent in tissue. According to certain embodiments, the therapeutic agent is delivered in a relatively concentrated form and diluted by the second material upon delivery of the second material. A gradient of the agent exists with the most concentrated form being present furthest from the needle track opening. For example, a concentrated dose of therapeutic agent may be delivered in a 10 microliter volume followed by a 90 microliter volume of a second material, such as PBS. As another example, the second material is optionally immiscible with the therapeutic agent, which may further enhance retention of the therapeutic agent in the tissue. For example, a concentrated bolus of aqueous plasmid DNA may optionally be followed with a 70% injection of ethanol.

The injection devices of the present invention may optionally include one or more pressure aprons and/or gaskets that are applied to one or more of the needle lumens to prevent or reduce loss of the therapeutic agent or second material through the needle track while the needle is in place.

According other embodiments of the present invention, injection devices are provided, which include an injection needle 9 (see for example, FIG. 5) at a distal end of an inner lumen 8 (which injection needle may be a taper or sharpening at the end of a tube forming the inner lumen) adapted to inject a therapeutic agent into tissue, an outer lumen 6 adapted to provide a vacuum seal between an injection needle and the needle track in tissue formed with the injection needle, and a vacuum-creating device (not shown) for creating a vacuum in the outer lumen.

According to these embodiments, therapeutic agent retention in the tissue is preferably improved by using an injection device that forms a seal between the outer surface of the injection needle and the tissue of the needle track. The seal is preferably formed by creating a negative pressure by the vacuum-creating device in a channel between one or more optional gaskets 7 that enter the needle track. According to these embodiments, the negative pressure in the second lumen created by the vacuum-creating device, pulls the tissue against the optional gaskets, thus substantially preventing the flow of the agent out of the needle track.

Suitable gaskets for use in the present invention would be known to those skilled in the art based on the present disclosure. The gaskets are preferably shaped and positioned on the device so as to improve the vacuum seal that will be formed between the needle and the tissue within the needle track. The gaskets may be made into many different geometrical shapes. Additionally, one or more gaskets may be integrated proximal or distal to the end of the outer lumen. The gaskets are preferably positioned on the outer walls of the inner lumen, near or on the needle portion of the lumen walls.

The gaskets according to the present invention may be a combination of two or more materials, which may be determined by those skilled in the art to attain a desired compliance, improve adhesion to the needle, and/or allow for easier penetration of the tissue. Gaskets are preferably made (at least in part) out of one or more biocompatible materials (such as silicone, polyethylene, teflon, PTFE, nylons, urethanes, epoxies, pebax, ABS, and polypropylene), even more preferably one or more compliant, biocompatible materials. The gaskets preferably resist shear forces associated with deployment of the needle into the myocardium. Additionally, a metal portion may be incorporated on the distal end of the gasket to facilitate penetration of the myocardium. Thus, the gaskets may include materials such as metal alloys, such as stainless steel, Nitinol, titanium, cobalt-chromium alloys, and the like or combinations thereof. The gaskets may be coated with one or more materials, such as hydrogel, cyano-acrylate or potassium metaphosphate polymers. According to certain embodiments, the surface of the gasket may be roughened to improve adhesion.

Embodiments of the present invention include injection devices including an injection needle at a distal end of an inner lumen, adapted to inject at least one therapeutic agent into tissue; and at least one compliant gasket having a shape and size such that when the gasket is situated between the injection needle and a needle track formed in tissue with the injection needle, a sufficient seal is formed between the needle and the needle track that when therapeutic agent is injected into tissue the gasket(s) reduce outflow from the needle track of therapeutic agent. In these embodiments, no outer lumen or vacuumcreating device is necessarily needed to form a seal between the needle and the needle track, but they are optional to try and form a more effective seal. In these embodiments, the non-coring nature of the needle will result in a force normal to the needle and gasket, thus, compressing the gasket. A more effective seal may be formed using the injection devices of these embodiments, by gaskets having a larger outer diameter. However, gaskets having a smaller diameter may cause less trauma to the tissue.

Figure 6:
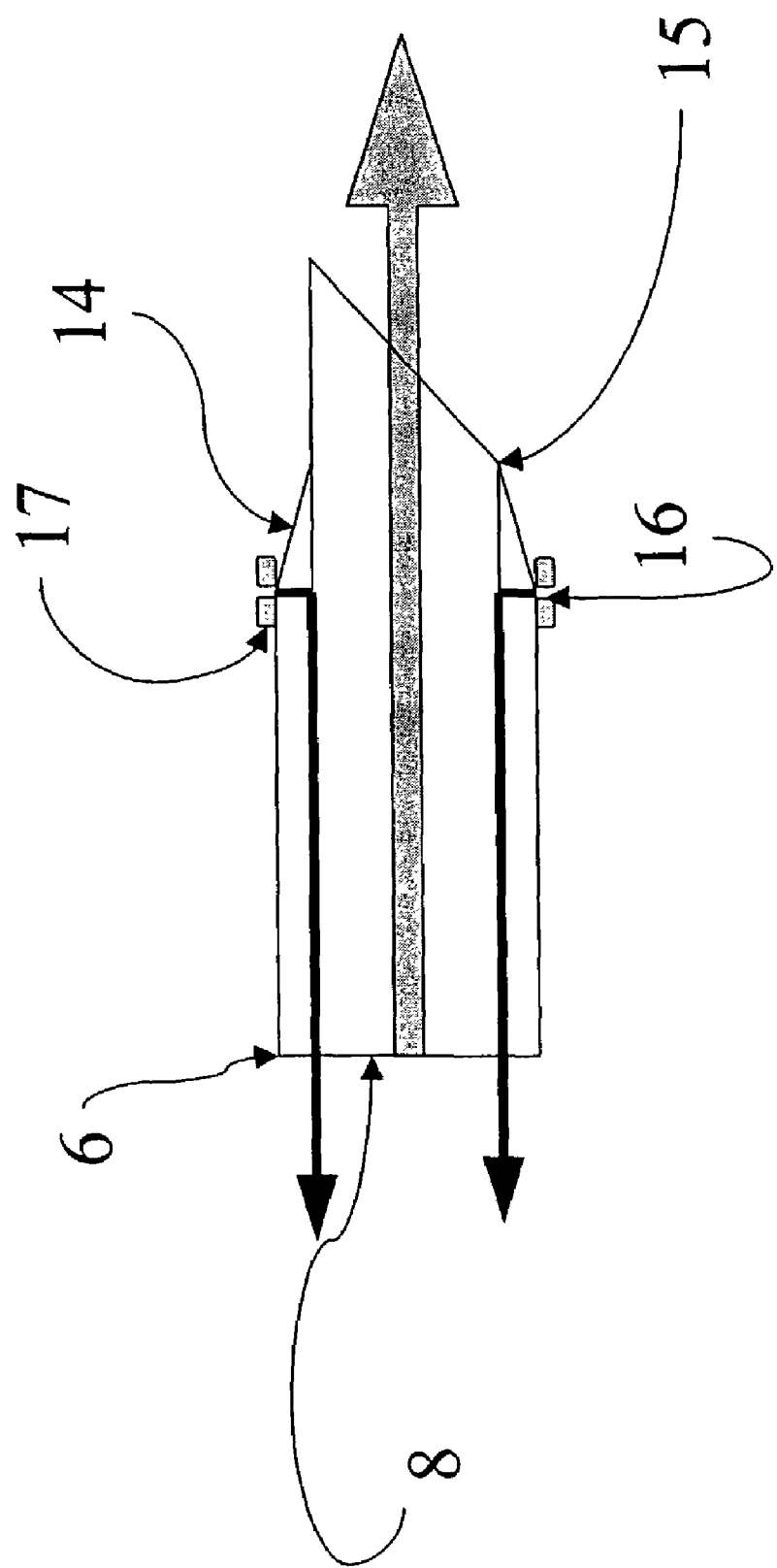
FIG. 6 is a sectional view of another embodiment of the invention. In this embodiment the walls of the outer lumen 6 have openings 16 to provide communication between the negative pressure created in the outer lumen and the needle track.
Figure 7:
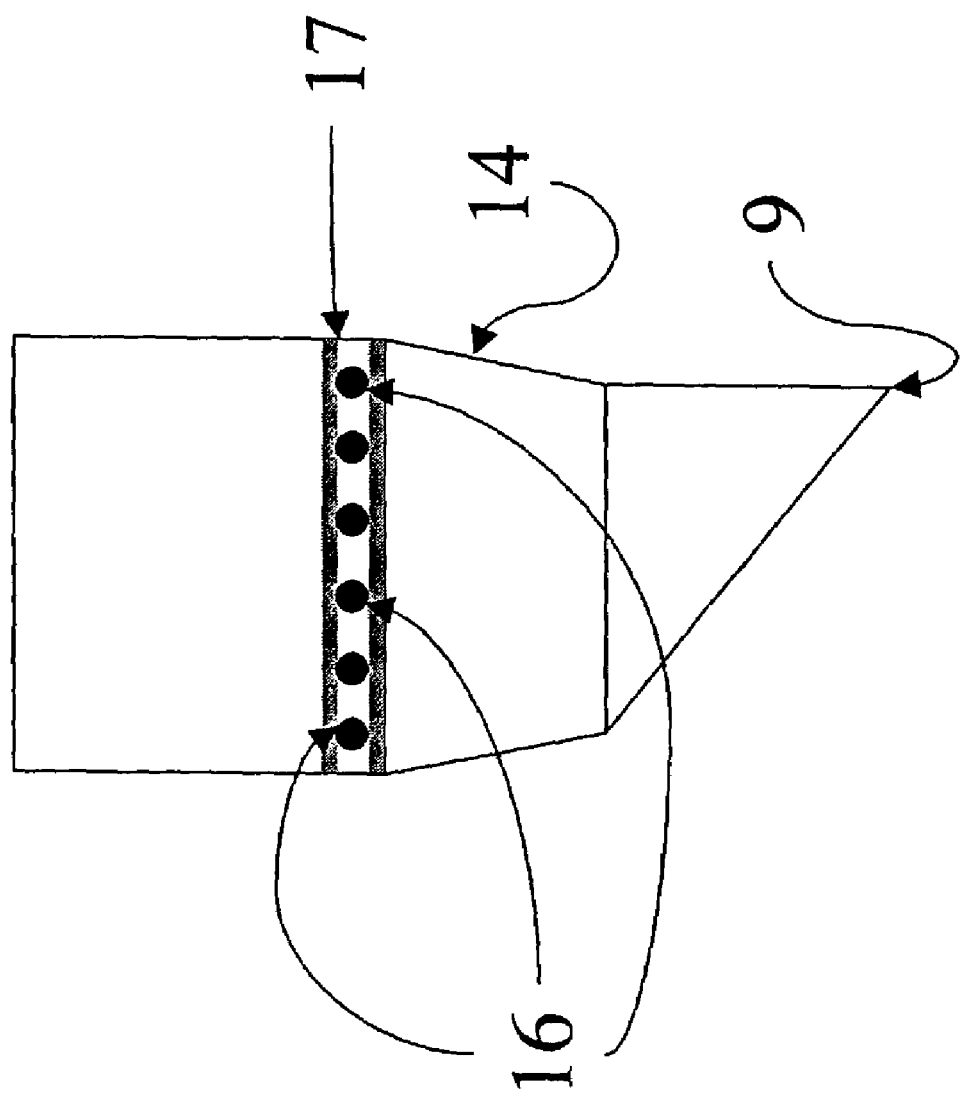
FIG. 7 shows a portion of the injection device of FIG. 6. This view shows the openings as being holes aligned substantially circumferentially, and further shows gaskets on two sides of the holes.

FIG. 6 depicts embodiments of the present invention in which the walls of the outer lumen form a tube or other shape that is tapered down at the end 14 to the inner lumen's outer walls 15 at the distal end. According to these embodiments, openings 16 provide communication between the outer lumen and the needle track (see also FIG. 7). Preferably, openings from the outer lumen to the needle track are formed by a series of holes aligned substantially circumferentially. Even more preferably, the holes are aligned in a somewhat continuous form and are positioned relatively distally on the injection device so as to make the outer lumen as stable as possible. Preferably at least one compliant gasket, preferably two compliant gaskets 17 are fixed proximal and distal to the openings 16. Additionally, preferably the walls of the distal end of the outer lumen are fixed to the outer surface of the inner lumen. This design allows for added stability of the distal end of the outer lumen.

Figure 8:
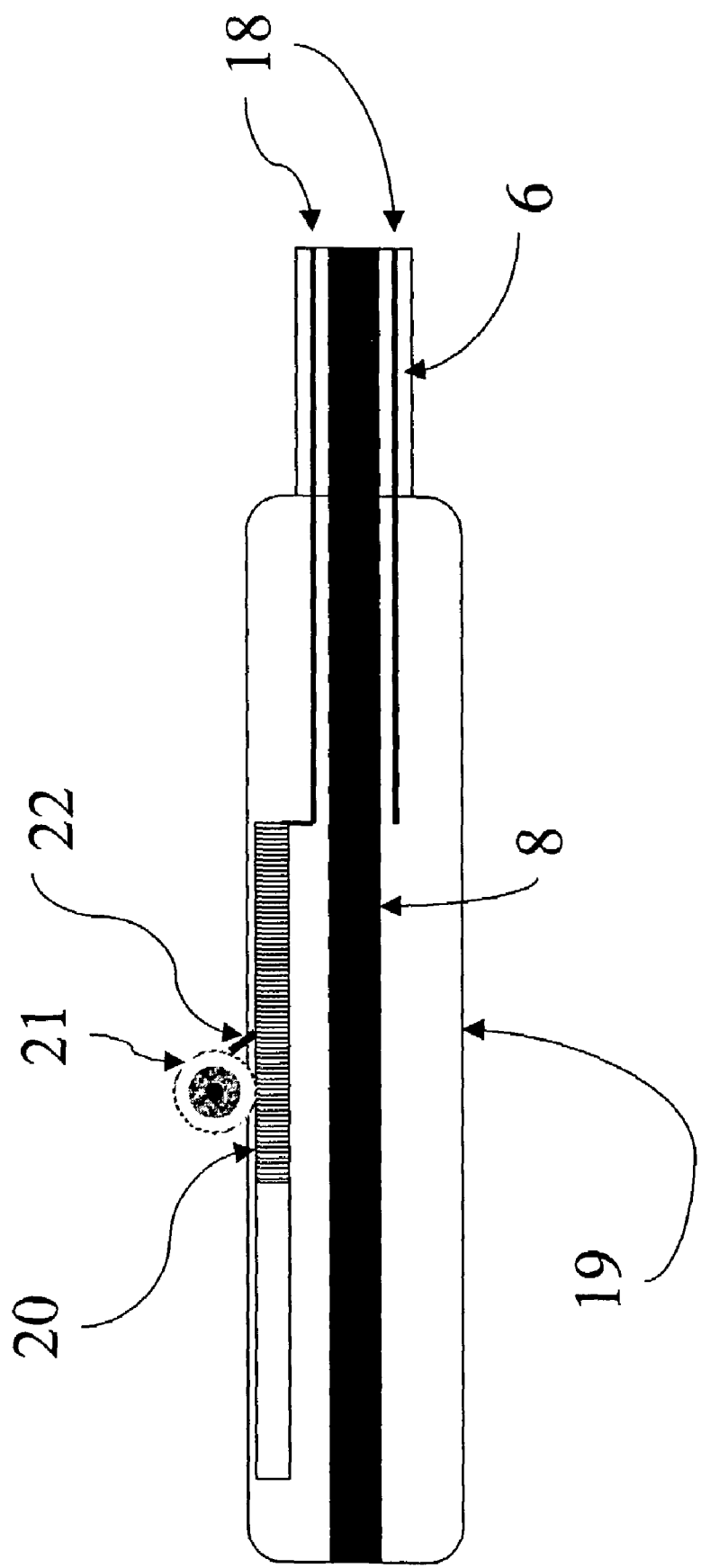
FIG. 8 is a sectional view of a catheter of the injection device (as in FIG. 6) meeting up with and being attached to a handle designed so as to create and maintain a negative pressure in the outer lumen of the device with a plunger 20 and ratchet 22.

According to these embodiments, the outer lumen preferably continues the length of the catheter and is connected to a cylindrical chamber 18 within a handle 19 as shown for example, in FIG. 8. Preferably the outer lumen 6 is connected to the cylindrical chamber 18. The inner lumen 8 continues through the handle 19 and is used to deliver the therapeutic agent. According to this embodiment, a plunger 20 within the chamber, is retracted with a thumb wheel 21 to create a negative pressure within the outer lumen. A ratchet 22 attached to the thumb wheel holds the plunger in place for the user while the agent is delivered through the inner lumen.

The injection devices of the present invention optionally include one or more pressure aprons. In embodiments having one or more pressure aprons, a small apron is attached to the needle such that as the needle is deployed the apron presses against and makes a seal within the needle track. Embodiments having such pressure aprons are particularly useful for example when the therapeutic agent (or carrier thereof) is a relatively viscous material.

Preferably, the injection devices of these embodiments of the present invention include at least one compliant gasket having a shape and size such that when the gasket is situated between the injection needle and the needle track and a vacuum is created in the outer lumen by the vacuum-creating device, the vacuum pulls tissue from the needle track against the gaskets, substantially preventing the therapeutic agent from flowing out of the needle track.

Walls of the outer lumen preferably form a tube that has a tapered distal end 10. The size and geometry of the outer lumen and its walls and the gaskets are selected such that they are sufficient to engage an inner wall of the needle track while minimizing additional trauma to the tissue.

The vacuum-creating device may be any suitable device known to those skilled in the art as being able to create a vacuum in a lumen, such as a plunger, vacuum pump, syringe, and the like. A non-limiting example of a vacuum pump that may be suitable for use in accordance with the present invention, is an 1180 Gomco suction unit. Preferably, the injection device of the present invention preferably has a device or portal within a proximal handle, which is used to create a vacuum by one controlling the vacuum-creating device.

According to preferred embodiments, injection devices of the present invention include an inner lumen adapted to inject a therapeutic agent into tissue, where walls of the inner lumen form a tube or other shape that has a tapered or sharpened distal end; an outer lumen adapted to provide a vacuum seal between the injection needle and a needle track in tissue formed with the inner lumen, wherein walls of the outer lumen form a tube or other shape that has a tapered distal end; and a vacuum-creating device adapted to create a vacuum in the outer lumen. According to these embodiments, the outer lumen is preferably shorter than the inner lumen, such that a distal end of the walls of the outer lumen is from about 0.1 mm to about 20 mm, preferably from about 1 mm to about 10 mm (which distance may vary depending on the tissue to be injected), from the tapered distal end of the inner lumen tube; and at least one compliant gasket is attached to an outside wall of the inner lumen. Alternatively, these lumens may also have various cross-sections including concentric circles and crescent moons.

Figure 5:
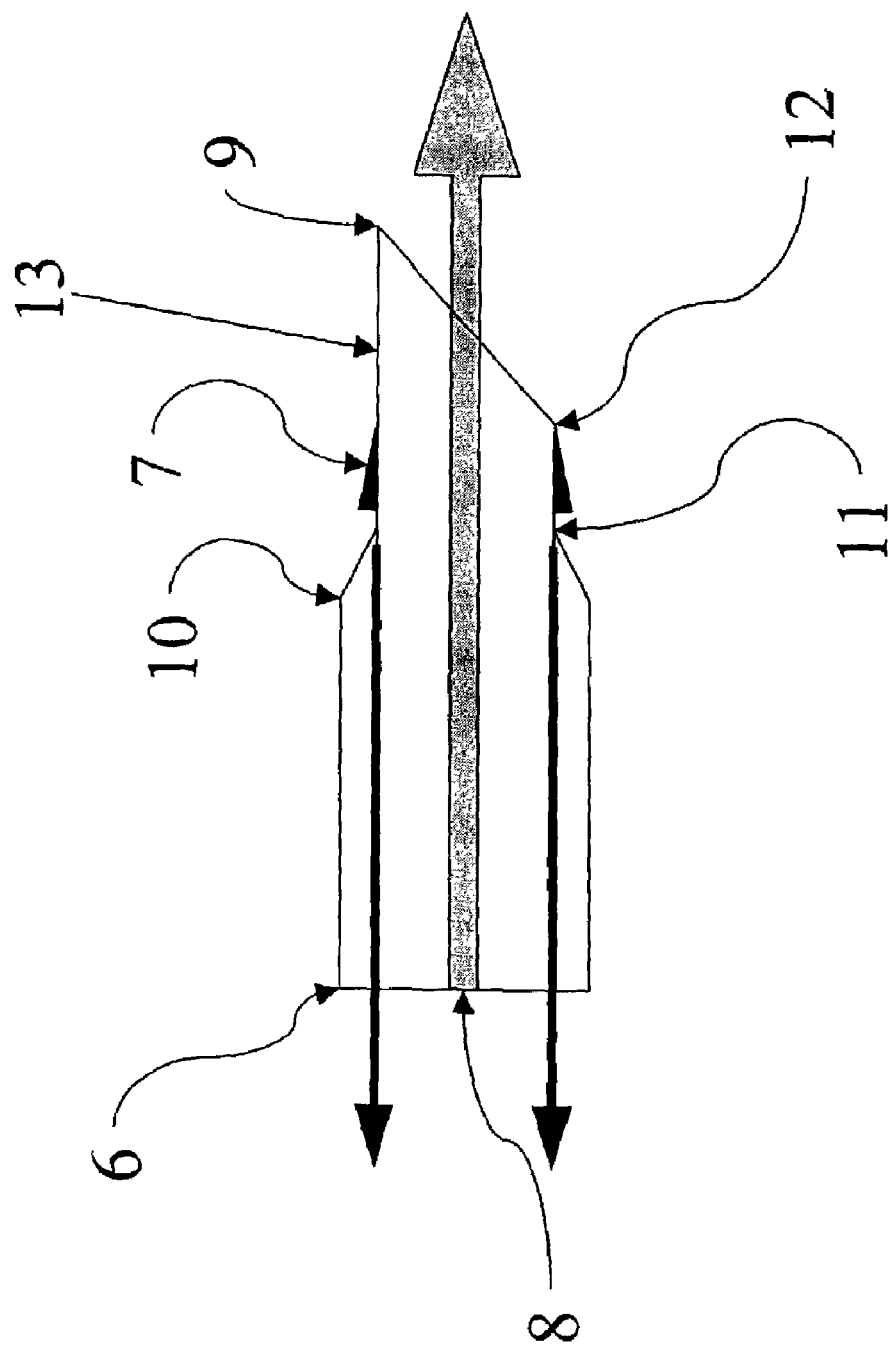
FIG. 5 depicts an injection device according to the present invention having an inner lumen 8 that contains therapeutic agent and an outer lumen 6 through which a vacuum may be formed. This embodiment also has gaskets 7.

FIG. 5 shows particularly preferred embodiments of the invention an injection catheter having a (inner) lumen 8 is within an outer lumen 6, wherein the outer lumen forms a tube having a tapered end 10. According to these embodiments, the outer lumen is shorter in length than the inner lumen, such that the distal end 11 of the outer lumen 6 (of FIG. 5) is a relatively short distance for example, from about 0.1 to about 20 mm, preferably from about 1 mm to about 10 mm, from the beginning of the tapered end 12 of the tube formed by the walls of the inner lumen. At least one tapered, preferably compliant, gasket 7 is attached to the outer wall of the inner lumen 13. According to these preferred embodiments, the proximal end of the gasket is preferably a relatively short distance (for example, from about 0.1 to about 5 mm) from the end 11 of the outer lumen 6. The distal end of the gasket may preferably substantially coincide with the beginning of the tapered end of the inner lumen 12. The device of these embodiments preferably has a handle that having a port such that a vacuum pump or syringe can be attached thereto to create a vacuum within the outer lumen. A valve is preferably incorporated into the port such that once an appropriate vacuum level is established, (for example less than 22 in. Hg, more preferably less than 25 in. Hg, depending on the altitude and other factors as would be apparent to those skilled in the art), it can be essentially maintained without continued manipulation of the pump or syringe. An embodiment of the present invention also preferably includes or is attached to a pressure gauge that indicates the level of vacuum within the outer lumen. The gauge may preferably be used to determine when an appropriate vacuum seal has been established and to indicate a failure in the seal.

According to other preferred embodiments, the end of the tapered or sharpened portion 9 or injection needle at the end of the inner lumen is selected or designed such that it will not core the tissue, but rather separate it. In particular, in the case injecting therapeutic agent into myocardium, as the myocardium exerts a force normal to the outer surface of the needle, one or more compliant gaskets are compressed and seal the more distal portion of the needle track from the more proximal portion. Deformation of the gasket(s) preferably decrease aspiration of the therapeutic agent into the outer lumen. Additionally, the normal force of the myocardium onto the outer surface of the needle or tapered end of the inner lumen preferably aid in the formation of the vacuum seal.

Methods of Delivering Therapeutic Agents

Further embodiments of the present invention relate to methods for delivering therapeutic agents to a tissue.

The present invention includes methods of delivering one or more therapeutic agents to tissue with an injection device. The methods include injecting a therapeutic agent into tissue, preferably tissue of a mammal, from a first lumen of an injection device and injecting a second material into the tissue from a second lumen of the injection device.

According to embodiments of the present invention, the present methods include injecting at least one therapeutic agent into tissue from a first lumen of an injection device and injecting at least one second material to the tissue from a second lumen of the injection device.

The therapeutic agent(s) and second material(s) are as described above with regard to injection devices of the present invention. The injection device is also preferably an injection device according to the embodiments described above. In particular, as described above, the spatial relationship of the lumens with respect to each other may be varied. Preferably, the first lumen is within the second lumen as depicted in FIG. 1. Each lumen may be controlled together or independently, but preferably independently, as described above.

The tissue to which a therapeutic agent is being delivered according to the present methods, is also as set forth above. According to preferred embodiments, the methods of the present invention include methods of delivering a therapeutic agent to a tissue of a mammal including injecting a therapeutic agent into tissue of a mammal in need of the therapeutic agent from a first lumen of an injection device, and injecting a second material to the tissue from a second lumen of the injection device. More preferably, the mammal is a human.

Injecting the second material to a tissue is intended to mean that the second material may be injected anywhere near or actually into the tissue. For example the second material may be injected in the tissue itself, proximately to the tissue or near the tissue, but not necessarily in the tissue. It may also mean that the second material is injected into a needle track that has already been formed in the tissue by injection of the therapeutic agent. This injection may include any form of injection via needle or non-needle methods. For example, when the second lumen is activated, the second material may be released into an area near the injection site of therapeutic agent and that would be considered "injecting a second material" within the scope of the present invention, so long as the step of injecting at least one second material is performed so as to achieve reduced outflow of the therapeutic agent from the tissue into which it is injected.

The second material is injected after, before or substantially simultaneously with the injection of the therapeutic agent, depending on various factors such as the composition and physical properties of the second material and the therapeutic agent, as described above.

According to embodiments of the present invention, the method further includes injecting a third material into a tissue from the third lumen of the injection device. The third lumen and third material may be as set forth above. The third material may be injected before, after or substantially simultaneously with the therapeutic agent or the second material.

According to preferred embodiments the third material and the second material form a solid or semi-solid plug when they contact one another.

Embodiments of the present invention may further include applying a pressure apron or gasket to one or more of the lumens, preferably to substantially prevent loss of the therapeutic agent through a needle track in the tissue.

The composition and amount of the second material and timing of its injection with respect to the injection of the therapeutic agent, are as described above and selected so as to reduce or preferably eliminate leakage of the therapeutic agent(s) from the injection site.

According to other embodiments of the present invention, methods of delivering therapeutic agent to tissue are provided that include creating a vacuum between an injection needle and the needle track it creates to avoid leakage of the therapeutic agent from the needle track. Methods according to these embodiments include positioning an injection device adjacent to tissue; deploying a needle at the distal end of the injection device into the tissue forming a needle track in the tissue; establishing a vacuum in an outer lumen of the injection device to create a vacuum seal between the needle track and the needle; injecting at least one therapeutic agent into the tissue from the inner lumen; and releasing the vacuum seal.

The injection devices, therapeutic agents, tissue to be injected, and other components of these methods are as described above with respect to the injection devices.

The vacuum may be established in the outer lumen by any method of forming a vacuum known to those skilled in the art. One method of establishing a vacuum includes opening a port valve associated with the outer lumen and using a vacuum-creating device to create a negative pressure. According to this method, the valve is then closed to maintain the vacuum in the outer lumen.

The methods of the present invention optionally include flushing the lumens with saline before deploying the needle into tissue.

The methods may also further include waiting for a period of time, such as from about 1 second to about 60 seconds, preferably about 2 to about 20 seconds, between injecting a therapeutic agent into the tissue and opening the port valve.

The diameter of the outer lumen may be selected such that it is large enough for vacuum purposes, but small enough to reduce potential trauma to the tissue caused by the size of the injection device.

In embodiments where the tissue being injected is myocardium, the myocardium preferably aids in the formation of the vacuum seal. As the myocardium contracts, the tissue forming the needle track pushes against the needle. Therefore, if a gap exists between the opening of the outer lumen and the needle track, it may close when the myocardium contracts. The needle track tissue may be caught by the steady flow created by the vacuum-creating device and the seal formed. Additionally, as the myocardium contracts, the needle may move creating trauma to the tissue. The vacuum seal within the needle track according to the methods of the present invention is advantageous in that it may act to stabilize the needle and reduce associated trauma.

Shear thinning and shear thickening are properties of some fluids that may be advantageous to the present invention. The fluid can be made more or less viscous by simply impeding its progress through a lumen—i.e., increasing friction. High viscosity materials will stay implanted better than those with low viscosity.

The methods of the present invention may optionally include other steps that may improve the delivery of therapeutic agents to a target site depending on various factors including for example, the method being employed to deliver the therapeutic agent and second material. Examples of such steps include keeping the injection device engaged with the tissue for a sufficient period of time after the injection has been completed (e.g., about 2 seconds to about 60 seconds) such that the therapeutic agent is substantially absorbed by the target tissue; using cryogenic techniques or electrosurgical techniques; and/or using a thickening agent, bioadhesive material or sealant.

According to certain embodiments of the invention, a thickening agent may be added to the therapeutic agent prior to injection, so as to increase the ability of the therapeutic agent to resist forces tending to push the therapeutic agent out of the tissue via the needle tracks.

As used herein, "thickening agent" refers to any biocompatible additive that results in an increased viscosity of the materials being injected. By way of example, suitable thickening agents include albumin, iohexol or other contrast agent, alginates, polyacrylic acid, hyaluronic acid, dextran, collagen, gelatin, polyethylene glycol, poloxamers, chitosan, SAIBER, PEG-PLGA, potassium metaphosphate polymers, and various biocompatible polymers.

Suitable biocompatible polymers for use in the present invention are hydrophilic or hydrophobic, and include, but are not limited to, polycarboxylic acids, cellulosic polymers, including cellulose acetate and cellulose nitrate, gelatin, polyvinylpyrrolidone, cross-linked polyvinylpyrrolidone, hydrogels, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, ethylene vinylacetate, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers.

In other embodiments of the present invention, the therapeutic agent and/or the second material or other materials being injected (in embodiments having second or other materials) further includes at least one bioadhesive material. As used herein, "bioadhesive material" refers to any biocompatible additive that results in an increase of the affinity of the injected material for tissue. Bioadhesive materials for use in conjunction with the invention include suitable bioadhesive materials known to those of ordinary skill in the art. By way of example, suitable bioadhesive materials include fibrinogen with or without thrombin, fibrin, fibropectin, elastin, laminin, cyano-acrylates, polyacrylic acid, polystyrene, potassium metaphosphate polymers, alginates, SAIBER, bioabsorbable and biostable polymers derivatized with sticky molecules such as arginine, glycine, and aspartic acid, and copolymers.

In other embodiments of the present invention, the method of the present invention further includes delivering at least one tissue sealant to substantially seal the mouth of the needle track upon needle removal. The sealant is delivered to the mouth of the needle track by any suitable means, such as through a lumen of a multi-lumen catheter, in which case the therapeutic agent is preferably delivered via a separate lumen. Alternatively, for example, the sealant may be added to the therapeutic agent being injected (or second or additional materials in embodiments containing such materials), or may be coated onto the exterior of the needle.

Such tissue sealants preferably include those having suitable bonding properties, elasticity and biodegradability for the tissue to which the sealant is to be applied. By way of example, suitable sealants include cyanoacrylates, collagen, fibrinogen with or without thrombin, fibrin, fibrin glue, fibropectin, elastin, laminin, cyano-acrylates, polyacrylic acid, polystyrene, potassium metaphosphate polymers, alginates, SAIBER, bioabsorbable and biostable polymers derivatized with sticky molecules such as arginine, glycine, and aspartic acid, and copolymers.

According to other embodiments of the present invention, at least one of the methods described above further includes sealing the injection site by performing radio frequency cautery at the mouth of the needle track to seal the mouth upon needle removal from the tissue. Cauterization involves using such intense heat to seal the open ends of the tissue. Radio frequency cautery may be performed by any suitable method.

According to other embodiments of the present invention, the present methods further include using resistance heating at the mouth of the needle track. Intense heat may be used to seal the mouth of the needle track upon needle removal. Intense heat used to seal open ends of tissue may be generated by a variety of different methods. In preferred embodiments, intense heat is generated by resistance heating a metallic probe, such that the generated heat is intense enough to seal the open ends of tissue.

The present methods may optionally include performing laser heating at the mouth of the needle track to seal the mouth upon needle removal to further inhibit outflow of the therapeutic agent. In these embodiments, laser emitted optical energy may be used to heat biological tissue to a degree suitable for denaturing the tissue proteins such that the collagenous elements of the tissue form a "biological glue" to seal the tissue.

According to other embodiments, the present methods optionally include plugging the mouth of a needle track with a solid plug or by coagulating one or more materials at the mouth upon needle removal. Examples of materials that may be used in accordance with these embodiments in order to seal the mouth of the needle track include fibrin glue, cyanoacrylate-based adhesives and the like. Other suitable sealant plugs would be apparent to those in the art based on the present disclosure. In preferred embodiments, the sealant plug may be heated (or cooled, depending on the temperature at which the material being used is liquid) prior to application to the mouth of the needle track, and subsequent cooling (or heating) may aid in solidifying and sealing the tissue. For example, a temperature sensitive polymer, which is liquid at above or below physiological temperature (i.e., about 37° C.) and solidifies at physiological temperature may be used in these embodiments. Examples of suitable materials for use in these embodiments include N-isoproylacrylamide and certain celluloses.

According other embodiments, the present methods optionally include applying a coagulating material to the mouth of the injection site while the material is in a first fluent state. Then the material is maintained in a position so as to plug the mouth of the injection site under conditions which convert the material in situ into a second less-fluent or essentially non-fluent state. The conversion may be achieved either by changing the environment surrounding the material by the addition or removal of chemicals or energy, or by passive means such as maintaining the material at the normal internal body temperature of a patient. The transition of the state of the material from a fluent state to a less fluent or essentially non-fluent state may be the result of a phase change or of a viscosity change or of polymerization.

Preferably the material of these embodiments is one or more biocompatible materials. In preferred embodiments the material is a polymeric material, which can be applied as polymers, monomers, macromers or combinations thereof The polymeric materials are preferably those materials that can be polymerized or have their viscosity altered in vivo, preferably by the application of light, ultrasound, radiation or chelation, alone or in the presence of added catalyst or by a change to physiological pH, by solvent dispersive systems, such as SAIBER and PEG-PLGA, difflusion of calcium ions (alginate) or borate ions (polyvinyl alcohol) into the polymer, or change in temperature to body temperature.

Examples of polymers that may be suitable for use in these embodiments include those polymers listed above as being suitable thickening agents. Examples of in situ polymerization include, but are not limited to, alginates crosslinked with multivalent cations, fibrinogen crosslinked with thrombin and photochemical crosslinking. Further examples of suitable polymers include the following. Materials which polymerize or alter viscosity as a function of temperature include poly(oxyalkene) polymers and copolymers such as poly(ethylene oxide)-poly(propylene oxide) (PEO-PPO) copolymers, and copolymers and blends of these polymers with polymers such as poly(alpha-hydroxy) acids, including but not limited to lactic, glycolic and hydroxybutyric acids, polycaprolactones, and polyvalerolactones. Examples of materials which polymerize in the presence of divalent ions such as calcium, barium, magnesium, copper, and iron include naturally occurring polymers collagen, fibrin, elastin, agarose, agar, polysaccharides such as hyaluronic acid, hyalobiuronic acid, heparin, cellulose, alginate, curdlan, chitin and chitosan, and derivatives thereof, cellulose acetate, carboxymethyl cellulose, hydroxymethyl cellulose, cellulose sulfate sodium salt, and ethylcellulose. Examples of materials that can be crosslinked photochemically with ultrasound or with radiation generally include those materials that contain a double bond or a triple bond; examples include monomers which are polymerized into poly(acrylic acids), poly(acrylates), polyacrylamides, polyvinyl alcohols, polyethylene glycols, and ethylene vinyl acetates. Examples of materials that can be crosslinked by the addition of covalent crosslinking agents, such as glutaraldehyde, succindialdehyde or carbodiimide, include amino containing polymers including polypeptides and proteins such as albumin and polyethyleneimine.

Alternatively, a non-polymeric coagulant may be used, wherein the non-polymeric material is capable of transfoining into a substantially solid matrix in situ is either added to the therapeutic agent prior to injection or applied to the mouth of a needle track after a needle is removed from tissue.

The non-polymeric material in these embodiments may optionally be combined with at least one organic solvent. Suitable organic solvents include those that are biocompatible, pharmaceutically-acceptable, and will at least partially dissolve the non-polymeric material. The organic solvent has a solubility in water ranging from miscible to dispersible. The solvent is capable of diffusing, dispersing, or leaching from the composition in situ into aqueous tissue fluid of the implant site such as blood serum, lymph, cerebral spinal fluid (CSF), saliva, and the like. Solvents that are useful include, for example, substituted heterocyclic compounds such as N-methyl-2-pyrrolidone (NMP) and 2-pyrrolidone (2-pyrol); esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as ethanol and propanol; polyhydroxy alcohols such as propylene glycol, polyethylene glycol (PEG), glycerin (glycerol), 1,3-butyleneglycol, and isopropylidene glycol; dialkylamides such as dimethylformamide and dimethylacetamide; dimethylsulfoxide (DMSO) and dimethylsulfone; tetrahydrofuran; lactones such as e-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof. Preferred solvents include N-methyl-2-pyrrolidone, 2-pyrrolidone, dimethylsulfoxide, ethyl lactate, propylene carbonate, glycofurol, glycerol, and isopropylidene glycol. Preferably the organic solvent is biocompatible and non-toxic.

A composition of the non-polymeric material is preferably flowable with a consistency that ranges from watery to slightly viscous to a putty or paste. The non-polymeric material eventually coagulates to a microporous, solid matrix upon the dissipation of the organic solvent into adjacent tissue fluids. The non-polymeric composition can be manipulated and shaped within the defect site as it solidifies. Advantageously, the moldability of the composition as it hardens allows it to conform to irregularities, crevices, cracks, holes, and the like, in the implant site. The resulting substantially solid matrix is preferably biodegradable, bioabsorbable, and/or bioerodible, and will be gradually absorbed into the surrounding tissue fluids, and become disintegrated through enzymatic, chemical and/or cellular hydrolytic action. The term "biodegradable" means that the non-polymeric material and/or matrix of the implant will degrade over time by the action of enzymes, by simple or enzymatically catalyzed hydrolytic action and/or by other similar mechanisms in the human body. The term "bioerodible" means that the implant matrix will erode or degrade over time due, at least in part, to contact with substances found in the surrounding tissue fluids, cellular action, and the like. By "bioabsorbable," it is meant that the non-polymeric matrix will be broken down and absorbed within the human body, for example, by a cell, a tissue, and the like.

Optionally, the composition of non-polymeric material of these embodiments can be combined with a minor amount of a biodegradable, bioabsorbable thermoplastic polymer such as a polylactide, polycaprolactone, polyglycolide, or copolymer thereof, to provide a more coherent solid implant or a composition with greater viscosity so as to hold it in place while it solidifies. The non-polymeric materials are also capable of coagulating or solidifying to form a solid implant matrix upon the dissipation, dispersement or leaching of the solvent component from the composition and contact of the non-polymeric material with an aqueous medium. The solid matrix has a firm consistency ranging from gelatinous to impressionable and moldable, to a hard, dense solid.

Non-polymeric materials according to these embodiments that are suitable for use in the present invention generally include any having the foregoing characteristics. Examples of useful non-polymeric materials include sterols such as cholesterol, stigmasterol, β-sitosterol, and estradiol; cholesteryl esters such as cholesteryl stearate; $C_{12}$–$C_{24}$ fatty acids such as lauric acid, myristic acid, palmitic acid, stearic acid, arachidic acid, behenic acid, and lignoceric acid; $C_{18}$–$C_{36}$ mono-, di-and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof, sucrose fatty acid esters such as sucrose distearate and sucrose palmitate; sorbitan fatty acid esters such as sorbitan monostearate, sorbitan monopalmitate and sorbitan tristearate; $C_{16}$–$C_{18}$ fatty alcohols such as cetyl alcohol, myristyl alcohol, stearyl alcohol, and cetostearyl alcohol, esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glycerol tristearate, stearic acid, stearic anhydride, glyceryl monooleate, glyceryl monolinoleate, and acetylated monoglycerides.

Any of the above-described second materials, thickening agents, bioadhesive materials, tissue sealants, solid plugs, or coagulants (including polymeric and non-polymeric coagulants), or compositions containing any of the above, may contain one or more additives.

The present invention will now be described in detail with respect to showing how certain specific representative embodiments of the needles and methods of the present invention, the apparatus components and process steps being understood as examples that are intended to be illustrative only. In particular, the invention is not intended to be limited to the physical orientation of injection device components, order of the steps and the like specifically recited herein.

EXAMPLE 1

An injection device is provided according to the present invention having an injection needle at a distal end of an inner lumen, adapted to inject at least one therapeutic agent into tissue, an outer lumen adapted to provide a vacuum seal between the injection needle and a needle track in tissue formed with the injection needle, and a vacuum-creating device for creating a vacuum in the outer lumen. The injection device further includes at least one compliant gasket.

Prior to use, both lumens of the device are flushed with saline. The injection needle is deployed once the distal end of the catheter is positioned substantially perpendicular to and in contact with endocardial wall. The port valve of the device is opened and a pump is used to establish a negative pressure in the outer lumen and a vacuum seal between the needle and the needle track it created upon deployment of the injection needle. A pressure gauge is used to determine when an appropriate seal is established. The injection device is moved slightly to aid in forming the seal.

The therapeutic agent is then injected into the tissue. The port valve is then opened, releasing the vacuum seal and the needle is retracted. The injection device is then repositioned for subsequent injections into a different position of the myocardium tissue.

While the present invention is described with respect to particular examples and preferred embodiments, it is understood that the present invention is not limited to these examples and embodiments. In particular, the present invention is not limited to the physical components of the injection devices listed herein so long as they contain at least two lumens where the second lumen is adapted to release a second material or the second lumen is adapted so as to create a vacuum, such that outflow of therapeutic agent from a needle track is reduced. Additionally, the types of therapeutic agents and second materials and the orientation and deployment of the lumens are not intended to be limited by the present examples.

Moreover, the present invention is not limited to the method steps recited herein and may contain additional steps, such as deploying additional lumens or adding additional ingredients to the therapeutic agent or other materials, as would be apparent to those skilled in the art based on the present disclosure so as to reduce outflow of therapeutic agent from tissue. Additionally, the present invention is not limited to the sequence of the method steps. In particular, different lumens may be deployed or activated at different times depending for example, on what material or agent is being deployed or injected or whether a vacuum is being created.

What is claimed is:

1. A therapeutic delivery system comprising:
a first lumen having a proximal end and a distal therapeutic delivery end; and
a second lumen having a proximal end and a distal orifice,
the first lumen slidable relative to the second lumen,
the second lumen slidable relative to the first lumen,
the distal therapeutic delivery end of the first lumen extendible past the distal orifice of the second lumen,
the distal orifice of the second lumen in fluid communication with an outside surface of the first lumen,
the distal therapeutic delivery end of the first lumen having a piercing portion
wherein a tissue sealing gasket is coupled to a surface of the first lumen and wherein the tissue sealing gasket has a tapered cross-section, a smaller portion of the tapered cross section being closer to the piercing portion than a larger portion of the tapered cross section.

2. A therapeutic delivery system comprising:
a first lumen having a proximal end and a distal therapeutic delivery end; and
a second lumen having a proximal end and a distal orifice,
the first lumen slidable relative to the second lumen,
the second lumen slidable relative to the first lumen,
the distal therapeutic delivery end of the first lumen extendible past the distal orifice of the second lumen,
the distal orifice of the second lumen in fluid communication with an outside surface of the first lumen,
the distal therapeutic delivery end of the first lumen having a piercing portion
wherein a tissue sealing gasket is coupled to a surface of the first lumen and
wherein a surface of the gasket is from about 1 mm to about 5 mm from the piercing end of the first lumen and the gasket contains a sloped surface mimicking a sloped surface on the second lumen.

3. The therapeutic delivery system of claim 2 wherein the second lumen is coupled to a vacuum source, the vacuum source creating a vacuum large enough to draw tissue, being delivered therapeutic by the system, towards and against an external surface of the first lumen.

4. A therapeutic delivery system comprising:
a first lumen having a proximal end and a distal therapeutic delivery end; and
a second lumen having a proximal end and a distal orifice,
the first lumen slidable relative to the second lumen,
the second lumen slidable relative to the first lumen,
the distal therapeutic delivery end of the first lumen extendible past the distal orifice of the second lumen,
the distal orifice of the second lumen in fluid communication with an outside surface of the first lumen,
the distal therapeutic delivery end of the first lumen having a piercing portion
wherein the second lumen is coupled to a vacuum source, the vacuum source creating a vacuum large enough to draw tissue, being delivered therapeutic by the system, towards and against an external surface of the first therapeutic delivery lumen and
wherein the vacuum source includes a plunger and a locking ratchet in communication with the plunger.

5. A therapeutic delivery system comprising:
a first lumen having a proximal end and a distal therapeutic delivery end; and
a second lumen having a proximal end and a distal orifice,
the first lumen slidable relative to the second lumen,
the second lumen slidable relative to the first lumen,
the distal therapeutic delivery end of the first lumen extendible past the distal orifice of the second lumen,
the distal orifice of the second lumen in fluid communication with an outside surface of the first lumen,
the distal therapeutic delivery end of the first lumen having a piercing portion
wherein a tissue sealing gasket is coupled to a surface of the first lumen and wherein the gasket is coated.

6. A therapeutic delivery system comprising:
a first lumen having a proximal end, a distal therapeutic delivery end, and a tissue sealing gasket coupled to a surface of the first lumen; and
a second lumen having a proximal end and a distal orifice,
the first lumen slidable relative to the second lumen,
the second lumen slidable relative to the first lumen,
the distal therapeutic delivery end of the first lumen extendible past the distal orifice of the second lumen,
the distal orifice of the second lumen in fluid communication with an outside surface of the first lumen when the delivery end of the first lumen is extending past the distal orifice of the second lumen,
the distal therapeutic delivery end of the first lumen having a piercing portion,
wherein a surface of the tissue sealing gasket is roughened.

7. A therapeutic delivery system comprising:
a first lumen having a proximal end and a distal therapeutic delivery end; and
a second lumen having a proximal end and a distal orifice,
the first lumen slidable relative to the second lumen,
the second lumen slidable relative to the first lumen,
the distal therapeutic delivery end of the first lumen extendible past the distal orifice of the second lumen,
an outside surface of the first lumen extendible past the distal orifice of the second lumen having a gasket coupled to the outside surface, the distal orifice of the second lumen in fluid communication with an outside surface of the first lumen, the distal therapeutic delivery end of the first lumen having a piercing end.

8. The therapeutic delivery system of claim 7 wherein the first lumen and the second lumen are coupled to one another.

9. The therapeutic delivery system of claim 7 wherein the second lumen is coupled to a vacuum source, the vacuum source creating a vacuum large enough to draw tissue being delivered therapeutic by the system towards and against the gasket.

10. The therapeutic delivery system of claim 7 wherein the first lumen is concentric with the second lumen.

11. The therapeutic delivery system of claim 7 wherein the gasket has a tapered cross-section.

* * * * *